(12) United States Patent
Kleiber et al.

(10) Patent No.: US 6,562,568 B1
(45) Date of Patent: May 13, 2003

(54) METHOD, KIT AND APPARATUS COMPRISING MAGNETIC GLASS PARTICLES FOR THE ISOLATION OF BIOMOLECULES

(75) Inventors: Jörg Kleiber, Penzberg (DE); Christine Markert-Hahn, Penzberg (DE); Herbert Harttig, Altrip (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/509,750
(22) PCT Filed: Sep. 29, 1998
(86) PCT No.: PCT/EP98/06196
§ 371 (c)(1),
(2), (4) Date: Sep. 5, 2000
(87) PCT Pub. No.: WO99/16781
PCT Pub. Date: Apr. 8, 1999

(30) Foreign Application Priority Data

Oct. 1, 1997 (DE) .......................................... 197 43 518

(51) Int. Cl.[7] .......................... C12Q 1/68; C12P 19/34; G01N 33/536; C07H 21/02; C07H 21/04
(52) U.S. Cl. .......................... 435/6; 435/91.1; 435/91.2; 435/287.2; 436/536; 536/23.1; 536/24.3; 536/24.31; 536/24.32; 536/24.33
(58) Field of Search .......................... 435/6, 91.1, 91.2, 435/287.2; 436/536

(56) References Cited

U.S. PATENT DOCUMENTS

| | | | |
|---|---|---|---|
| 5,206,568 A | * 4/1993 | Bjornson et al. | 318/568.1 |
| 5,234,809 A | 8/1993 | Boom et al. | |
| 5,443,791 A | * 8/1995 | Cathcart et al. | 422/65 |
| 5,665,554 A | * 9/1997 | Reeve et al. | 435/6 |
| 5,972,721 A | * 10/1999 | Bruno et al. | 436/529 |
| 6,027,945 A | 2/2000 | Smith et al. | |
| 6,136,083 A | 10/2000 | Schmidt et al. | |
| 6,296,937 B2 | 10/2001 | Pryor et al. | |
| 6,368,800 B1 | 4/2002 | Smith et al. | |

FOREIGN PATENT DOCUMENTS

| | | |
|---|---|---|
| EP | 0 757 106 A2 | 2/1997 |
| WO | WO 88/06533 | 9/1988 |
| WO | WO 88/06633 | 9/1988 |
| WO | WO 96/41811 | 12/1996 |
| WO | WO-9641811 A1 * | 12/1996 |
| WO | WO 97/10331 | 3/1997 |
| WO | WO 97/10359 | 3/1997 |
| WO | WO 99/67371 | 12/1999 |

OTHER PUBLICATIONS

Boom et al, "Rapid and Simple Method for Purification of Nucleic Acids", *Journal of Clinical Microbiology*, 1990, 28: 495–503.

BioRobot 9600 "The BioRobot 9600—An Integrated, compact workstation for nucleic acid purification", Qiagen Product Guide (1997) 100–103.

Ishida et al., "Development on full automatic DNA, RNA and Plasmid Extraction Instrument Using Unique Magnetic Particles Isolation Technology", Toyobo Product Information.

Merel et al., "Completely automated extraction of DNA from whole blood", *Clin Chem*, (1996) 1285–6.

* cited by examiner

*Primary Examiner*—Jeffrey Siew
(74) *Attorney, Agent, or Firm*—Charles M. Doyle; George C. Jen; Pennie & Edmonds LLP

(57) ABSTRACT

The invention concerns a process for preparing biological samples for the subsequent detection of an analyte. In particular, the invention relates to a process for the isolation of a nucleic acid in a sample using a suspension of magnetic glass particles. In addition, kits and apparatuses containing magnetic glass particles for sample preparation are provided.

27 Claims, 6 Drawing Sheets

US 6,562,568 B1

METHOD, KIT AND APPARATUS COMPRISING MAGNETIC GLASS PARTICLES FOR THE ISOLATION OF BIOMOLECULES

FIELD OF THE INVENTION

The invention concerns a process for preparing biological samples for the subsequent detection of an analyte, in particular a nucleic acid, in this sample. In addition reagent kits and new devices for sample preparation and new magnetic pigments are provided.

BACKGROUND ART

The sample preparation often has to meet special requirements in a method for the detection of an analyte in a biological sample. On the one hand, the analyte is often present at a very low concentration and, on the other hand, there are often many other substances in the sample which can interfere with the isolation or determination of the analyte.

WO 96/41811 discloses a process for the isolation of an analyte, especially a nucleic acid, from a biological sample wherein the sample which contains the analyte in a liquid is contacted with magnetic particles that have an outer glass surface which is essentially free of pores or has pores with a diameter of <10 nm, under conditions such that the analyte binds to the particle surface and the bound analyte is separated from the sample liquid. The process described in WO 96/46811 is very well suited to the purification of an analyte from a biological sample. However, it cannot be easily applied to an automated sample preparation.

Boom et al. (J. Clin. Microbiol. 28 (1990), 495–503) also describe a protocol for the purification of nucleic acids from a biological sample using silicon oxide particles fractionated according to size. However, this process is complicated and not suitable for automation and moreover there is a risk of carry-over.

In a method described in EP-A-0 757 106 for the extraction of nucleic acids, a sample is lysed, the nucleic acids present in the sample are bound to superparamagnetic metal particles, these are removed from the sample vessel with a pipette and thus separated from the other sample components. A disadvantage of this method is that losses may occur due to the necessity of having to remove the analyte from the sample with a pipette. Furthermore there is a risk of carry-over and contamination due to the use of several reaction vessels.

SUMMARY OF THE INVENTION

Hence the object of the present invention was to provide a new sample preparation process in which the disadvantages of the state of the art are at least partially eliminated. In particular it should be possible to automate the new process and have a temperature profile that is as simple as possible.

This object is achieved by a process for the isolation of an analyte from a biological sample comprising the steps:
(a) lysing the sample in a reaction vessel,
(b) adding a solid adsorption matrix
(c) incubating under such conditions that the analyte binds to the adsorption matrix,
(d) removing non-bound sample components from the reaction vessel,
(e) incubating under such conditions that the analyte is eluted from the adsorption matrix and
(f) separating the eluate from the adsorption matrix.

A further aspect of the present invention is a process for the isolation of an analyte from a biological sample comprising the steps:
(a) lysing the sample in a reaction vessel,
(b) adding a solid adsorption matrix,
(c) incubating under such conditions that the analyte binds to the adsorption matrix,
(d) separating non-bound sample components from the adsorption matrix,
(e) incubating under such conditions that the analyte is eluted from the adsorption matrix and
(f) separating the eluate from the adsorption matrix wherein at least steps (c) and (d) are carried out at essentially the same temperature.

DETAILED DESCRIPTION OF THE INVENTION

The process according to the invention is based on the selective binding of analytes to a solid adsorption matrix in the presence of a sample lysing buffer in which the analyte that is preferably a nucleic acid such as DNA e.g. chromosomal DNA, fragmented chromosomal DNA, plasmid DNA, viral DNA etc. or RNA e.g. mRNA, tRNA, rRNA or viral RNA etc., is separated from impurities of the sample such as proteins or cell debris. The sample can be any biological sample e.g. a body fluid such as blood, plasma, urine etc., a tissue sample, a sample of cultured cells or such like.

The adsorption matrix used in the process according to the invention is able to ensure the substantially selective binding of the analyte under the reaction conditions. A particulate adsorption matrix is preferably used which preferably contains a glass surface. Magnetic glass particles are particularly preferred, especially the magnetic particles described in WO 96/41811 with an external glass surface which is essentially free of pores or has pores with a diameter of less than 10 nm. Ferromagnetic particles are particularly preferred which have a particle size between 10 and 60 $\mu$m. Such particles can for example contain a core made of mica and magnetic particles immobilized thereon which is enclosed by a layer of glass. Whereas in WO 96/41811 the magnetic particles are placed in the individual reaction vessels in a solid form e.g. as tablets or a powder, the magnetic particles are preferably used according to the invention in the form of a suspension. Alcoholic suspensions having a concentration of about 5 to 20 mg/ml have proven to be particularly suitable. It was surprisingly found that, despite the high specific density of the magnetic glass particles, the suspension can be very reproducibly drawn out of a storage container which enables the process to be automated.

Although the glass particles described in WO 96/41811 give good results in the process according to the invention, particularly good results are obtained with glass particles whose glass phase contains the following metal oxides: $SiO_2$, $B_2O_3$, alkali metal oxide e.g. $K_2O$ or/and $Na_2O$ and optionally $Al_2O_3$ and an alkaline earth metal oxide e.g. CaO. The contents of these metal oxides are preferably as follows: 50 to 95 mol-% $SiO_2$, 0.2 to 30 mol-% $B_2O_3$, 0 to 10 mol-% $Al_2O_3$, 0 to 20 mol-% alkaline earth metal oxide and 0.2 to 20 mol-% alkali metal oxide where the percentages are each based on the total weight of the glass phase.

A glass phase which contains $SiO_2$, $B_2O_3$, $K_2O$, $Al_2O_3$ and CaO has proven to be particularly suitable for the isolation of RNA. A glass phase which contains $SiO_2$, $B_2O_3$ and $Na_2O$ has proven to be particularly suitable for the isolation of DNA.

In the process according to the invention the adsorption matrix is preferably added in an amount which corresponds to the minimum amount required to quantitatively bind the analyte present in the sample, in particular a nucleic acid, or the amount is somewhat larger, preferably at most 50% and particularly preferably at most 20% above this amount. The expected amount of nucleic acid in various type of samples can—if it is not already known—be determined in advance by common techniques e.g. phenol/chloroform extraction and subsequent measurement of the optical density.

Step (a) of the process according to the invention comprises lysing the sample in a reaction vessel. This lysis is usually carried out by lysing the cells present in the sample under denaturing conditions e.g. by adding a protease and a denaturing buffer. Proteinase K, pronase, elastase or/and lysozyme are preferably used as the proteinase. The use of proteinase K is particularly preferred.

The protease digestion is carried out in a denaturing buffer which contains a chaotropic compound e.g. urea or urea derivatives, preferably a chaotropic salt, particularly preferably a guanidinium salt such as guanidinium hydrochloride (especially for the isolation of DNA) or guanidinium thiocyanate (especially for the isolation of RNA) or a perchlorate or iodide. Concentrations in the range of 1 to 3 mol/l are preferred for guanidinium salts.

In contrast to the method described in WO 96/41811 for sample preparation, the solid adsorption matrix is only added after lysing the sample. This procedure results in a significantly lower unspecific binding of undesired sample components, e.g. proteins, to the adsorption matrix.

According to step (c) the analyte is selectively bound to the adsorption matrix by incubation in the lysing buffer preferably under chaotropic conditions.

Step (d) of the process according to the invention comprises the separation of non-bound sample components from the adsorption matrix. For this purpose the non-bound sample components are preferably removed from the reaction vessel. This can be achieved by adding and removing a wash buffer, optionally several times, which preferably contains a quantity of at least 50% (v/v) and particularly preferably of at least 60% (v/v) of a solvent that is miscible with water such as ethanol, propanol and acetone.

Steps (c), (d) or/and (e) of the process according to the invention are preferably carried out while mixing continuously or at intervals (i.e. mixing phases alternate with phases in which the reaction vessel is at rest) without adding external means. This mixing is preferably carried out by rotating the reaction vessel around its longitudinal axis while reversing the direction of rotation several times. The mixing vessel is particularly preferably rotated exactly around its longitudinal axis and the change in the direction of rotation is carried out such that the meniscus deflection of the liquid remains below a predetermined cut-off value. Such mixing processes are described in WO 91/15768 and EP-A-0 435 481.

The duration of steps (c) or/and (e) is preferably 20 min at most and comprises a continuous mixing or an interval mixing in short cycles, preferably in short cycles of preferably two minutes maximum. Particularly good results were obtained by interval mixing in a one minute cycle comprising 20 sec mixing and 40 sec resting.

When magnetic particles are used as an adsorption matrix it is possible to add liquids to the reaction vessel or aspirate liquids from the reaction vessel while mixing continuously, and the particles are held in the reaction vessel during the aspiration process. This mixing procedure allows the process according to the invention to be adjusted flexibly to suit various types of sample.

Furthermore it ensures that there is always a homogeneous distribution of the magnetic particles in the liquid phase.

Step (e) of the process according to the invention comprises the elution of the analyte from the adsorption matrix. A low salt buffer that is essentially free of organic solvents can be used for this as is known from the prior art. However, it was surprisingly found that the elution buffer can contain additional reagents such as enzymes e.g. enzymes used to manipulate nucleic acids such as RNases, DNases, restriction endonucleases, ligases, terminal transferases or/and polymerases. If the analyte is for example a DNA it is possible to add a DNase-free RNase during the elution in order to reduce the content of undesired RNA. On the other hand if the analyte is RNA, it is possible to add an RNase-free DNase during the elution. Other enzymes such as restriction endonucleases etc. can be added in an analogous manner. If the nucleic acid isolated by the process according to the invention is subjected to a subsequent amplification, a nucleic acid amplification master mix which contains the amplification buffer, nucleotides, primers, polymerase and buffer salts can also be added during the elution.

Step (f) of the process according to the invention comprises separating the eluate from the adsorption matrix. This separation can be carried out in the usual manner e.g. by sedimentation but preferably by magnetic separation.

The analytes isolated by the process according to the invention can be subsequently processed further in a known manner e.g., in the case of nucleic acids by amplification and subsequent detection, or detection without previous amplification or sequencing. For this purpose various analytes can be determined in aliquots of the eluate e.g. various viruses such as HIV, HCV and HBV.

An important feature of the process according to the invention is that many or optionally even all steps can be carried out at essentially the same temperature i.e. within a temperature range of ±2.5° C. This temperature is preferably in the range of room temperature to 70° C., particular preferably from room temperature to 40° C., most preferably at room temperature i.e. ca. 18 to 32° C. In a preferred embodiment of the process according to the invention at least the steps (c) of adsorption and (d) of washing are carried out at this temperature. Other steps, in particular the steps (a) of lysing or/and (e) of elution are particularly preferably also carried out at this temperature. The entire sample preparation can for example be carried out at a uniform temperature for the determination of HIV in blood samples. Optionally an additional after-treatment step at an elevated temperature can take place after step (f) of the process according to the invention which improves the amplification yields for certain analytes. It may be necessary for other analytes to carry out the pre-treatment or/and the elution at an elevated temperature. In this case the elevated temperature is preferably in the range of more than 40° C. to 95° C. e.g. ca. 70° C.

The process according to the invention is preferably carried out in an automated device. Examples of such devices are described in the following. It is also preferable that in the process according to the invention for sample preparation at least steps (a) to (e) are carried out in a single reaction vessel i.e. that there is no transfer into another reaction vessel. This considerably simplifies the process and also leads to a reduction of the risk of contamination.

Yet a further subject matter of the invention is a reagent kit which is especially suitable for carrying out the process described above comprising (a) a protease, (b) a sample lysing buffer, (c) a wash buffer, (d) an elution buffer and (e) a suspension of magnetic glass particles.

Yet an additional subject matter of the invention is a reagent kit for isolating DNA comprising magnetic glass particles whose glass phase contains $SiO_2$, $B_2O_3$ and $Na_2O$ and a reagent kit for isolating RNA comprising magnetic glass particles whose glass phase contains $SiO_2$, $B_2O_3$, $Al_2O_3$, CaO and $Ka_2O$.

Finally another subject matter of the present invention is a device for isolating an analyte from a biological sample comprising:

a sample preparation device (1), a holding device for reagents (2), a first holding device for reaction vessels for sample preparation (3) which is equipped for an operating temperature of $\leq 70°$ C., in particular $\leq 40°$ C., a second holding device for reaction vessels (4a, 4b, 4c), which optionally contains a cooling or/and heating means, and a robotic tool device (5).

The device according to the invention is preferably designed such that a single reaction vessel is used to carry out the 4 main steps of sample preparation i.e. lysis of a sample, adsorption of the released analyte e.g. a nucleic acid to a solid adsorption matrix e.g. magnetic glass particles, washing the adsorption matrix and eluting the analyte from the adsorption matrix.

The device is designed such that the first holding device for holding the reaction vessels for sample preparation is used at least for the adsorption of the analyte to the solid adsorption matrix and for washing the adsorption matrix. In a preferred embodiment the first holding device is also used for the sample lysis or/and for the elution of the analyte from the adsorption matrix. The reaction vessels for the sample preparation have a volume of preferably at least 1 ml. e.g. 1–5 ml.

The second holding device is designed for reaction vessels to store or/and further process the analyte e.g. PCR vessels which usually have a different shape than the reaction vessels used for the sample preparation. The reaction vessels for storing or/and additional processing have a volume of preferably up to 500 µl, e.g. 50–200 µl. Furthermore the second holding device can contain vessels for reagents which are required to process the sample containing the analyte e.g. a PCR master mix.

The device according to the invention can be designed such that one or several steps of the sample preparation or/and an after-treatment step can be carried out at an elevated temperature in the second holding device. For this purpose the second holding device can be designed to hold reaction vessels for at least one treatment step which is selected from lysing the sample, eluting the sample from the adsorption matrix and an after-treatment step after elution.

The first holding device preferably contains means for the magnetic separation. In addition it is preferable that the first holding device contains means for mixing the reaction vessels in particular by rotating them around their longitudinal axis. Such means can optionally be provided for the second holding device.

The robotic tool generally comprises automatic pipetting devices and optionally means for transporting reaction vessels e.g. between the first and second holding device. In addition a cap opening and closing unit may be integrated.

Special embodiments of inventive devices are shown in detail in the following. In the embodiment shown in FIG. 1 the sample preparation device (1) contains a holding device for reagents (2), a holding device for reaction vessels for sample preparation (3) with the functions mixing and magnetic separation which provides a temperature of preferably $\leq 40°$ C. and particularly preferably room temperature. The device additionally contains a holding station for further reaction vessels (4a) e.g. for PCR vessels which has a temperature of 4° C. to room temperature. The device additionally contains automated devices for pipetting and handling reaction vessels (5) which enables movements in an X, Y and Z direction. In this embodiment of the device according to the invention the four main steps of sample preparation i.e. lysis, adsorption, washing and elution take place in a single reaction vessel in the first holding device. Eluates are stored and further reagents e.g. PCR master mix are added in the second holding device. For further processing e.g. for a subsequent PCR, the vessels are transferred to an appropriate device e.g. a thermocycler (not shown).

In the embodiment shown in FIG. 2 the device contains a second holding device (4b) which is designed to hold reaction vessels for further processing e.g. PCR vessels and is equipped to set a temperature of 4° C. (cooling the PCR master mix) to 95° C. to heat the eluate after elution from the adsorption matrix. A cap counter-heating is preferred to prevent condensation on the cap of the PCR vessels.

The embodiment of the device according to the invention shown in FIG. 3 is provided with a second holding device for reaction vessels (4c) which is designed to hold PCR vessels or sample preparation vessels. In this second holding device cooling e.g. to 4° C. and heating e.g. to 95° C. is possible to heat the lysate or/and the eluate. Also in this case a cap counter-heating is provided to prevent condensation on the cap of reaction vessels.

In a further embodiment of the present invention (not shown) the first holding device is designed to set a temperature in the range of $\leq 70°$ C. The second holding device is—as shown in FIG. 3—suitable for cooling and heating sample processing and sample preparation vessels.

The devices according to the invention can be used especially in a process as described above.

BRIEF DESCRIPTION OF THE DRAWINGS

The present application is additionally elucidated in more detail by the figures and examples.

EXAMPLES

1. Preparation of Magnetic Glass Particles

Figure 1:
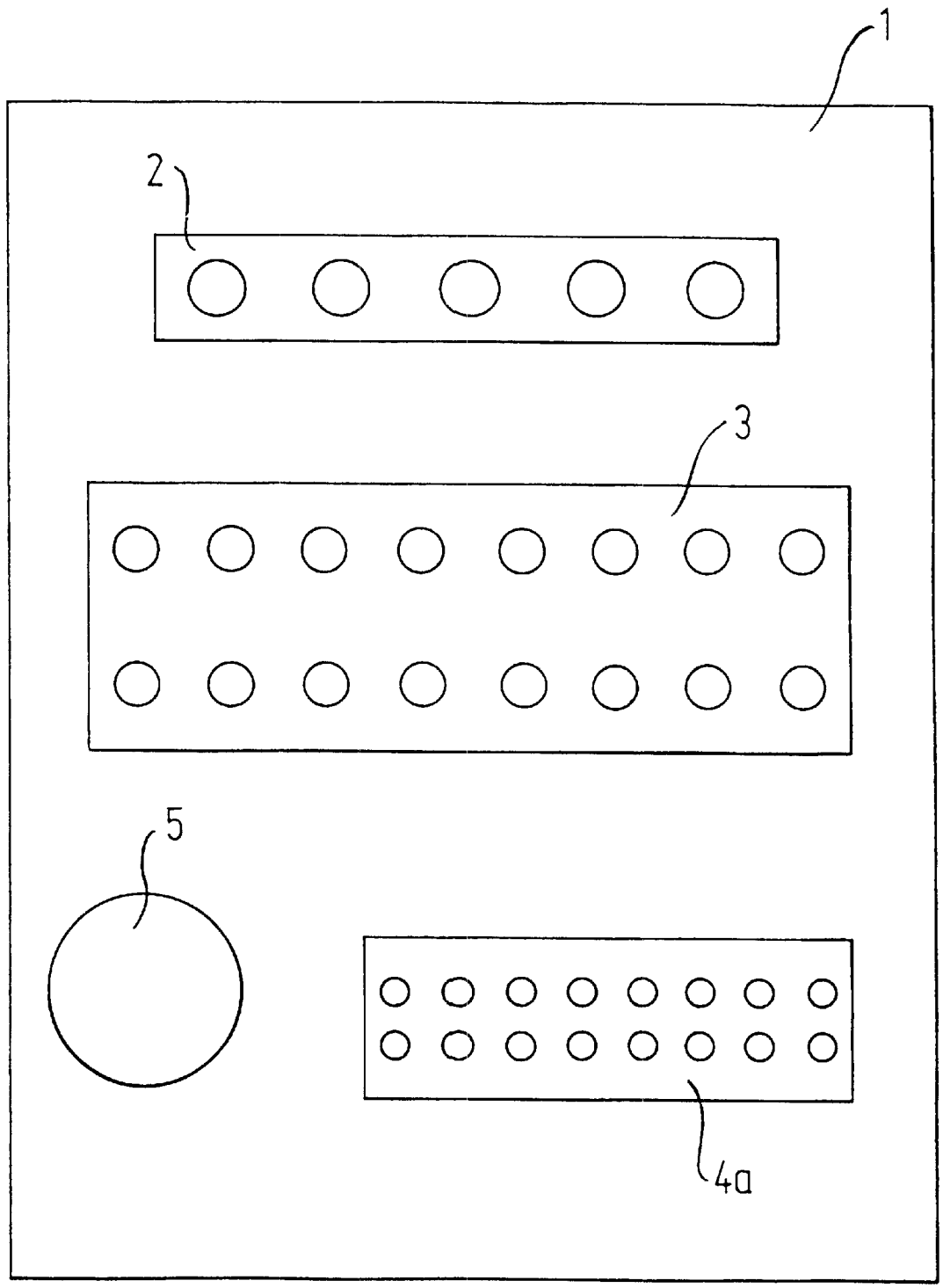
FIG. 1 shows a schematic representation of a first embodiment of the device according to the invention.
Figure 2:
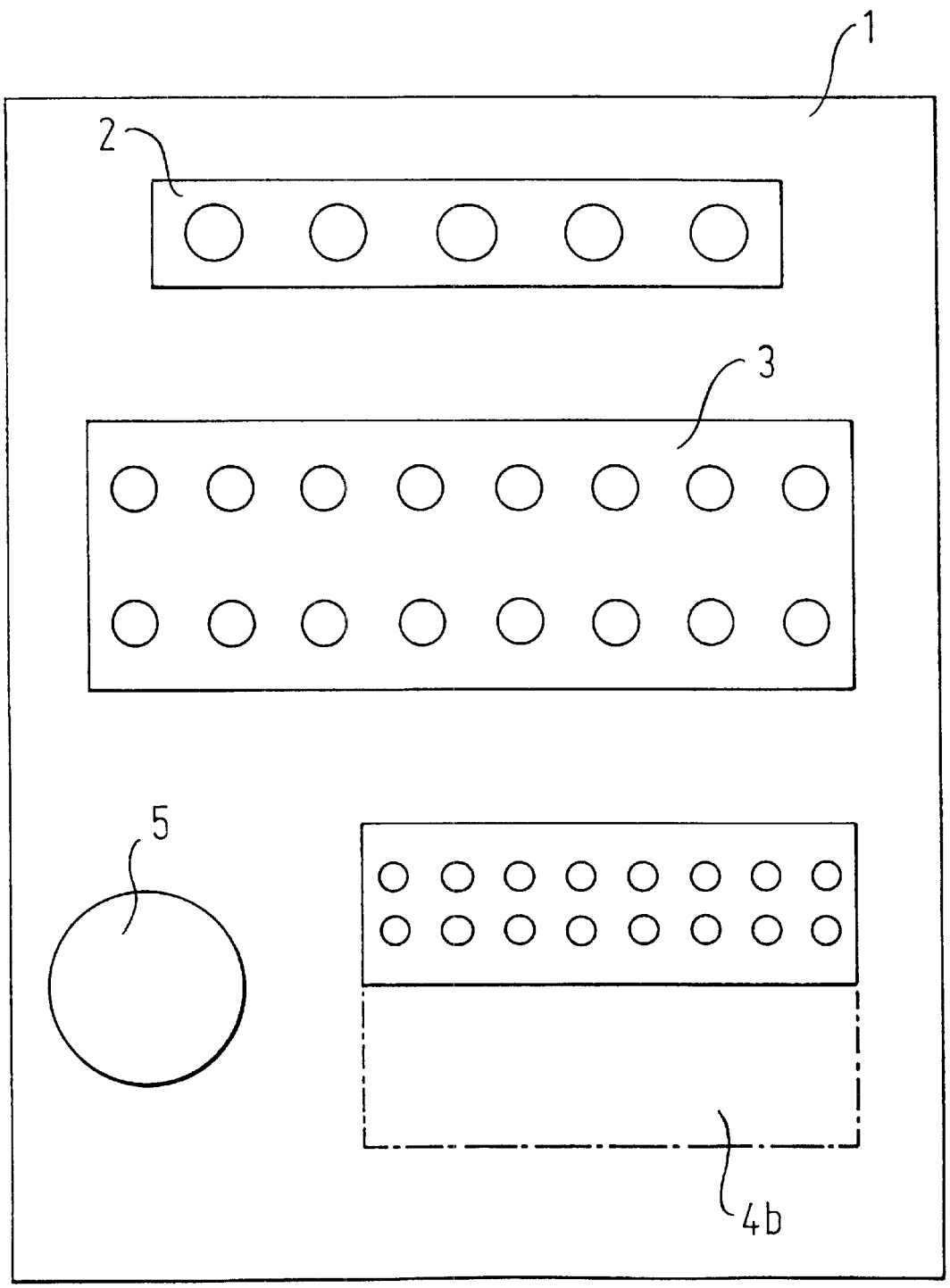
FIG. 2 shows a schematic representation of a second embodiment of the device according to the invention.
Figure 3:
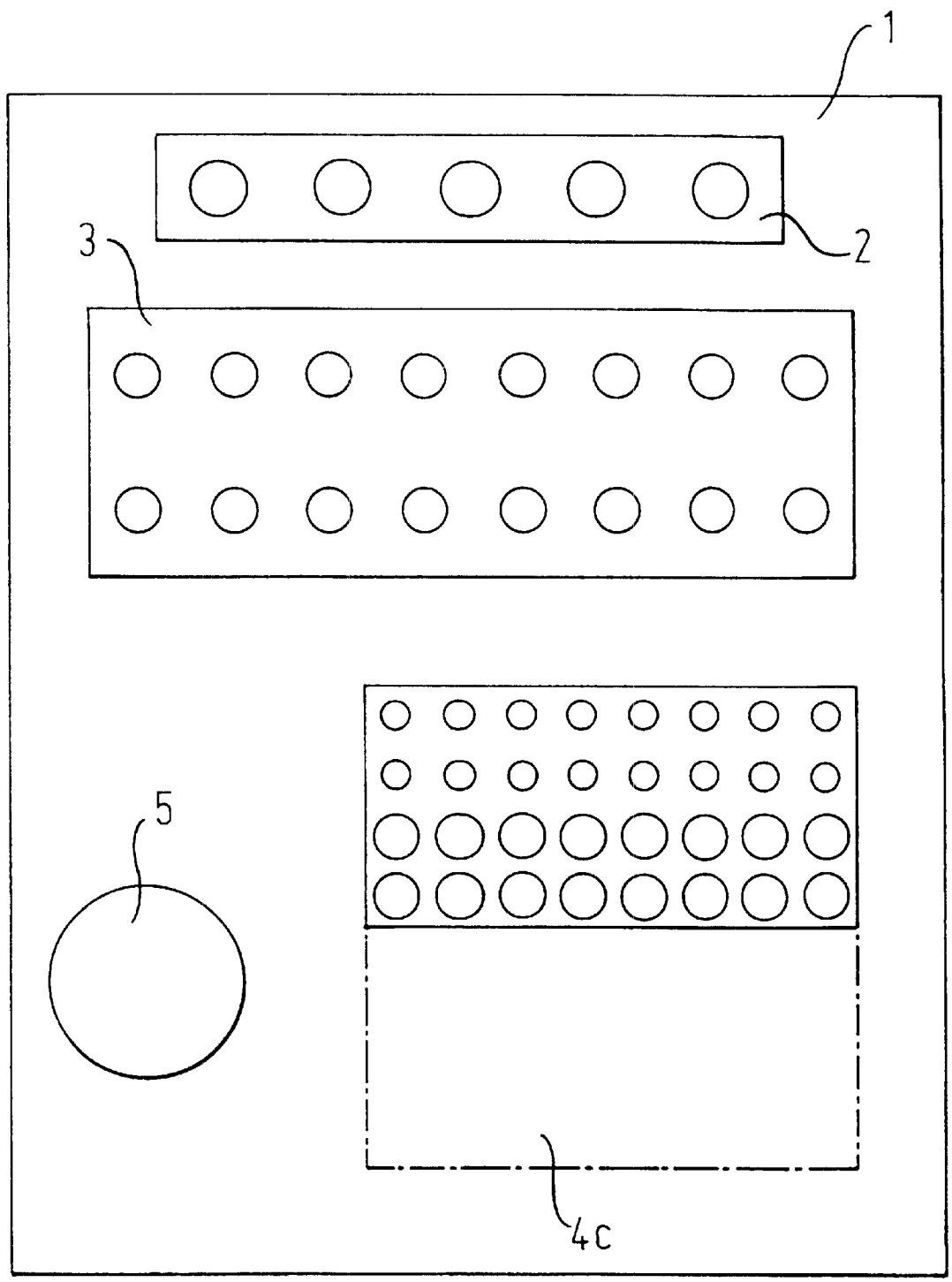
FIG. 3 shows a schematic representation of a third embodiment of the device according to the invention.

Two different sols were used. The sols were prepared as follows:

Sol 1: ($SiO_2$:$B_2O_3$:$Na_2O$=40:8:2)

Alcoholates of the oxides were stirred together in the above molar ratios analogously to the procedure in examples 1 and 2 of WO96/41811 to form a homogeneous phase. However, a deviation was that no HCl was used.

Subsequently 30 g iriodin 600 Black Mica (Merk) in 100 ml sol was stirred in.

Sol 2: ($SiO_2$:$B_2O_3$:$K_2O$:$Al_2O_3$:CaO=76:15:5:2:2)

Alcoholates of the oxides were stirred together in the above molar ratios analogously to the procedure in examples 1 and 2 of WO96/41811 to form a homogeneous phase. However, a deviation was that no HCl was used.

Subsequently 30 g iriodin 600 Black Mica (Merk) in 100 ml sol was stirred in.

The sols were subsequently subjected to a spray drying process.

The powder obtained by the spray drying was subjected to a separation of fines by sedimentation, a temperature treatment under a nitrogen atmosphere (60 l/h volume flow rate) at a heating rate of 1 K/min and kept for one hour at a compaction temperature in the range of 600 to 700° C. Subsequently the oven was cooled to 300° C. and flushed with oxygen for 1 h at this temperature. After cooling to room temperature the magnetic glass particles were removed and sieved through a 50 $\mu$m sieve to separate the coarse material.

The magnetic glass particles obtained from sol 1 are particularly suitable for the isolation of DNA. The glass particles obtained from sol 2 are particularly suitable for the isolation of RNA.

2. Standard Protocol for Sample Preparation for the Isolation of Nucleic Acids e.g. DNA The following standard protocol is suitable for isolating nucleic acids from biological samples such as whole blood or cultured cells. The nucleic acids obtained in this manner can be used directly after the elution for an amplification by PCR, a restriction cleavage or a Southern blot.

The reaction kit contains:
1. binding buffer (4.7 mol/l guanidinium hydrochloride, 10 mmol/l urea, 10 mmol/l Tris HCl, 20% Triton®X-100, pH 5.7
2. lyophilized proteinase K (dissolved in $H_2O$ to a concentration of 20 mg/ml)
3. wash buffer (56% (v/v) ethanol, 20 mmol/l NaCl, 10 mmol/l Tris HCl, pH 7.5)
4. elution buffer (10 mmol/l Tris pH 8.5)
5. magnetic glass particles, (MPG)
    a) tablets each containing 7.5 mg of the glass particles or
    b) 15% suspension of the glass particles in ethanol The kit components are stable and can be stored at room temperature. After dissolving proteinase K in water, the solution should be aliquoted and stored at −20° C. The frozen solution is stable for 12 months.

Standard Protocol
1. 200 $\mu$l sample is added to a 2 ml reaction vessel and admixed with 200 $\mu$l binding buffer and 40 $\mu$l proteinase K solution. It is subsequently incubated for 10 min. The incubation is preferably carried out at room temperature. However, under certain circumstances the incubation temperature can also be increased to up to 70° C.
2. After the incubation 200 $\mu$l isopropanol and an MGP tablet (or alternatively 200 $\mu$l MGP suspension) is added and incubated for 5 min at room temperature.
3. The reaction vessel is placed in a magnetic particle separator (Boehringer Mannheim, Cat. No. 1 641 794) and separated for about 1 min.
4. The supernatant is discarded and the reaction vessels are removed from the MP separator.
5. After addition of 500 $\mu$l wash buffer, the contents of the reaction vessel are mixed and again placed in the MP separator for about 1 min.
6. The supernatant is discarded. Step 5 is repeated three times. After the last washing process the remaining wash buffer is completely removed.
7. For the elution 100 $\mu$l of elution buffer which is optionally preheated to 70° C. is added. It is then mixed and incubated for 5 minutes at room temperature. The sample is placed in the MP separator and the supernatant is transferred into a clean reaction vessel.
8. The nucleic acids e.g. DNA obtained in this manner are stable and can be subsequently directly processed further or stored at 4° C.

The above protocol can also be used correspondingly for microtitre plates e.g. deep well microtitre plates (e.g. Ritter, J.J. Bioanalytic).

3. Chlamydia Trachomates DNA Detection by PCR 3.1 Manual Standard Protocol for Sample Preparation 200 $\mu$l of a urine sample and 240 $\mu$l binding buffer/proteinase K solution (5:1) are pipetted into a 2 ml reaction vessel, subjected to vortex mixing and incubated for 10 min at 70° C. Then the sample is cooled for 5 min to room temperature.

200 $\mu$l isopropanolic MGP solution is added to the sample by pipette. Immediately afterwards it is vortex mixed. The sample is then incubated for 15 min in a mixer e.g. Thermomixer 5436 (Eppendorf).

The MGPs are concentrated by transferring the sample to a magnetic separator. After one minute the supernatant is completely removed by pipette.

0.5 ml wash buffer is added to the MGPs by pipette. The sample is subjected to vortex mixing and then transferred to the magnetic separator. The supernatant is removed by pipette after 1 min. The washing procedure is repeated for a further two times.

200 ml elution buffer is added to the MGP. The sample is incubated for 10 min at 70° C. in a thermomixer at 1400 rpm. Condensed water is collected by briefly centrifuging. The sample is transferred to the magnetic separator and after 1 min 180 $\mu$l eluate is removed. The eluate is pipetted into a new reaction vessel and stored at 4° C. (for a storage period of <24 h) or at −20° C. (for a longer storage period).

50 $\mu$l eluate is used for the PCR: The evaluation is by electrochemiluminescence.

3.2 Protocol for a Semiautomated Process

Figure 4:
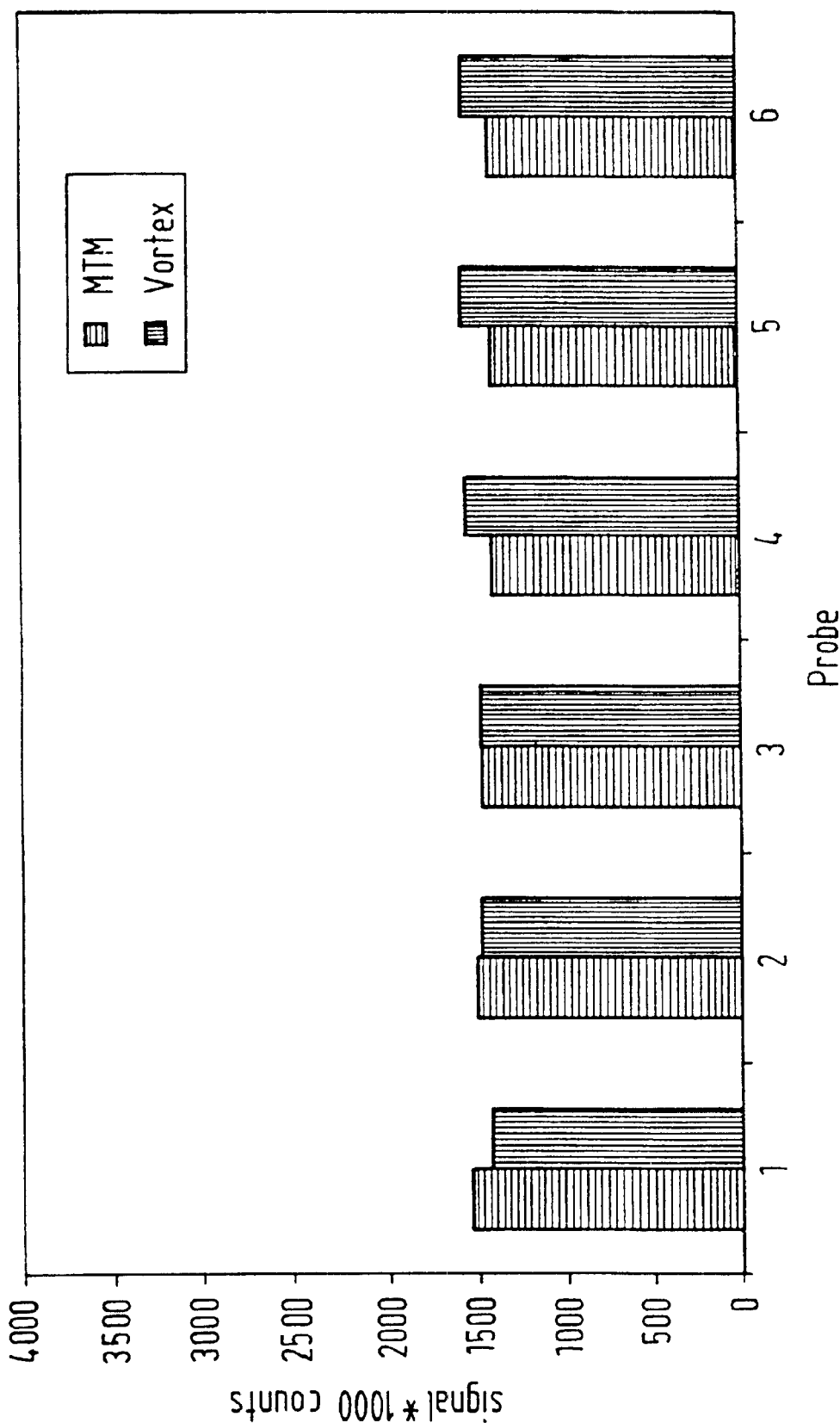
FIG. 4 shows the result of a chlamydia detection by PCR using manual and semiautomatic sample preparation.

Instead of the vortex mixing described in 3.1 and heating on a thermoblock, a semiautomated process is carried out in which the mixing and heating take place on a mixing and heating module. FIG. 4 shows a comparison of the determination of chlamydia. (sample: 100 elementary antibodies per 100 ml urine; six-fold determination) between the manual standard protocol (vortex) and the semiautomated process (MTM). It can be seen that the sensitivity is not impaired by the automation.

3.3 Semiautomated Protocol at Room Temperature

The sample preparation is carried out as described in section 3.2. However, the lysis and elution are carried out at room temperature.

3.4 Semiautomated Sample Preparation Protocol at Room Temperature With Subsequent After treatment of the Elulate The sample preparation is carried out as described in section 3.3. After elution an incubation is carried out for 10 min at 70° C.

Figure 5:
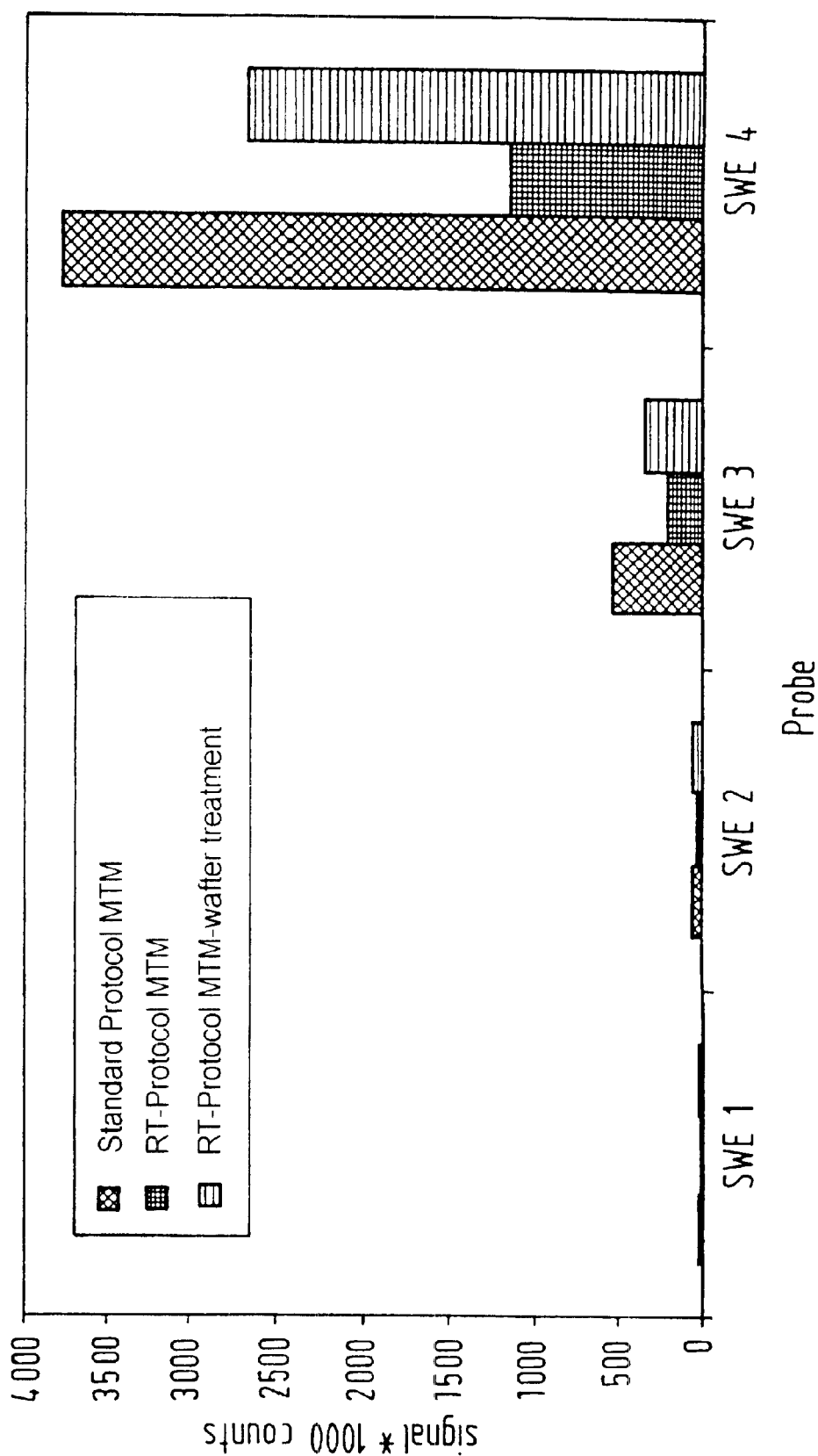
FIG. 5 shows the result of a chlamydia detection by PCR using semiautomatic sample preparation and various temperature profiles during the sample preparation.

FIG. 5 shows a comparison of the chlamydia determination (samples: SWE1, O chlamydia elementary antibodies (EAB) per ml urine, SWE2: 10 EAB, SWE3: 100 EAB and SWE4:1000 EAB each per ml urine) between the sample preparation protocols described in sections 3.2, 3.3 and 3.4. It can be seen that the standard protocol is more sensitive compared to a sample preparation at room temperature (RT protocol MTM) for the determination of chlamydia. However, the results of the sample preparation at room temperature and subsequent aftertreatment of the eluate (RT protocol MTM with aftertreatment) show that this effect can be largely compensated. It is therefore surprising that a temperature step is not necessary during the sample preparation per se.

This finding allows the sample preparation process to be considerably simplified since the steps of lysis, adsorption, washing and elution can be carried out at temperatures of $\leq 40°$ C. which simplifies an automation since a cap counter-heating and temperature regulation are not necessary.

4. HIV-RNA Detection by PCR

4.1 Manual Standard Protocol for Sample Preparation

Frozen plasma is thawed for 5 min at 37° C. and cooled on ice for further processing.

50 $\mu$l of a proteinase K solution (25 mg/ml) is pipetted into a 1.5 ml Sarstedt reaction vessel. 250 $\mu$l sample is added to this and mixed in a vortex mixer. Then 300 $\mu$l lysis buffer is added and it is again vortex mixed.

It is incubated for 10 min at room temperature on an Eppendorf mixer at 13,000 rpm. Then 300 $\mu$l of a MGP suspension (6 mg/ml MGP in isopropanol) is added, vortex mixed and incubated for 20 min at room temperature with continued mixing. The MGPs are separated on a magnetic separator and the supernatant is completely removed.

750 $\mu$l wash buffer is added to the MGPs. The MGPs are resuspended and separated as described previously. The wash procedure is repeated four times and the washing buffer is carefully removed at the end.

Then 100 $\mu$l elution buffer is added and the MGPs are resuspended. After 15 minutes incubation at 80° C. on an Eppendorf thermomixer (13,000 rpm), 90 $\mu$l eluate is transferred into a new reaction vessel. 40 $\mu$l eluate is used for the subsequent HIV determination by RT-PCR.

4.2 Semiautomated Standard Protocol for Sample Preparation

The sample preparation is carried out as described in section 4.1 except that the mixing and heating was carried out on a mixing and heating module.

4.3 Semiautomated Protocol at Room Temperature

The sample preparation is essentially carried out as described in section 4.2 except that all steps are carried out at room temperature. The incubation period for lysis, adsorption and elution is in each case 15 min.

Figure 6:
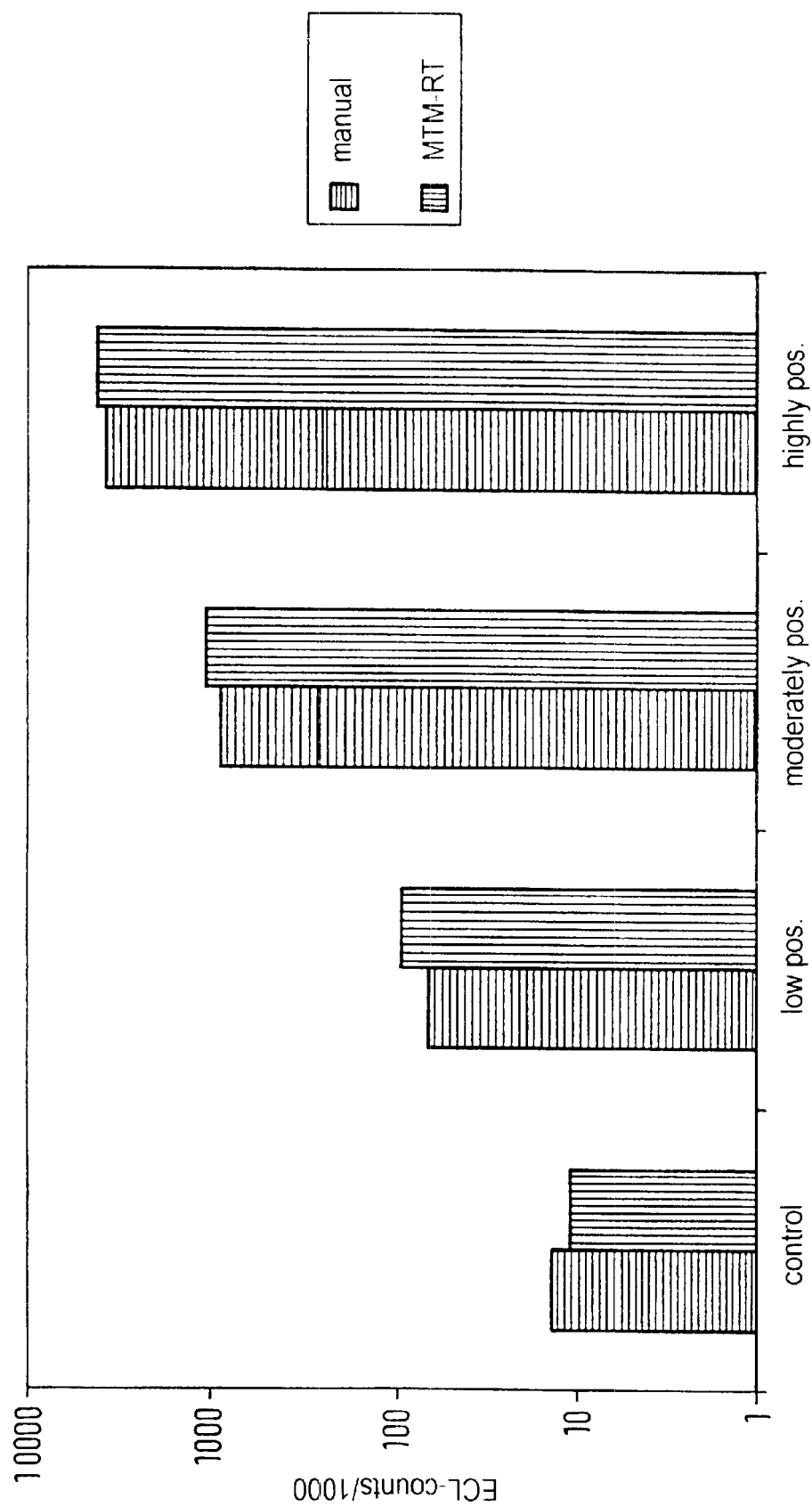
FIG. 6 shows the result of a HIV detection by PCR using manual sample preparation (standard protocol) and semiautomated sample preparation at room temperature.

It can be seen in FIG. 6 that the automation and the sample preparation at room temperature (RT protocol MTM) do not impair the sensitivity compared to the standard protocol with manual sample preparation (manual). Reproducible results are obtained for negative, low positive, moderately positive and highly positive plasma samples.

What is claimed is:

1. A process for the isolation of a nucleic acid analyte from a biological sample comprising the steps:
    (a) adding a suspension of magnetic glass particles in isopropanol to the lysed biological sample in a reaction vessel,
    (b) incubating under such conditions that the analyte binds to the magnetic glass particles,
    (c) removing non-bound sample components from the reaction vessel,
    (d) incubating under such conditions that the analyte is eluted from the magnetic glass particles, and
    (e) separating the eluate from the magnetic glass particles.

2. The process of claim 1, wherein step (a) comprises adding a protease and a denaturing buffer.

3. The process of claim 2, wherein the protease is proteinase K.

4. The process of claim 2, wherein the denaturing buffer contains a guanidinium salt.

5. The process of claim 1, wherein the magnetic glass particles comprise $SiO_2$, $B_2O_3$ and $Na_2O$.

6. The process of claim 1, wherein the amount of the magnetic glass particles added is at most 50% more than the amount that is required to quantitatively bind the analyte present in the sample.

7. The process of claim 1, wherein a continuous or intermittent mixing without adding external devices is carried out at least during step (b), (c) or (d).

8. The process of claim 7, wherein the mixing is achieved by rotating the reaction vessel around its longitudinal axis.

9. The process of claim 7, wherein the maximum period for carrying out step (b) or (d) is 20 min in each case.

10. The process of claim 1, wherein step (d) comprises adding and aspirating a wash buffer which is optionally repeated several times.

11. The process of claim 10, wherein the content of the wash buffer contains at least 50% (v/v) of an organic solvent that is miscible with water.

12. The process of claim 1, wherein an additional reagent is added in step (d).

13. The process of claim 1, wherein a low salt buffer is used for elution in step (e).

14. The process of claim 1, wherein a nucleic acid amplification master mix is added for elution in step (e).

15. The process of claim 1, wherein at least steps (a) to (d) are carried out at essentially the same temperature in the range from room temperature to 40° C.

16. The process of claim 1, wherein an additional step at an elevated temperature is carried out after step (f).

17. The process of claim 16, wherein the elevated temperature is in the range from more than 40° C. to 95° C.

18. The process of claim 1, wherein the process is carried out in an automated apparatus.

19. The process of claim 1, wherein steps (a) to (e) are carried out in a single reaction vessel.

20. A kit for isolating a nucleic acid analyte comprising
    (a) a protease,
    (b) a sample lysing buffer,
    (c) a wash buffer,
    (d) an elution buffer and
    (e) a suspension of magnetic glass particles in isopropanol.

21. The kit of claim 20, wherein the magnetic glass particles comprise $SiO_2$, $B_2O_3$ and $Na_2O$.

22. The kit of claim 20, wherein the magnetic glass particles comprise $SiO_2$, $B_2O_3$, $Al_2O_3$, $CaO$ and $K_2O$.

23. The process of claim 4, wherein the guanidinium salt is guanidinium hydrochloride or guanidinium thiocyanate.

24. The process of claim 1, wherein the glass particles comprise $SiO_2$, $B_2O_3$, $dAl_2O_3$, $CaO$ and $K_2O$.

25. The process of claim 12, wherein the additional reagent is an enzyme.

26. The method of claim 1, wherein the step of adding the suspension of magnetic glass particles in isopropanol is performed by an automatic pipetting device.

27. A process for the isolation of a nucleic acid analyte from a lysed biological sample comprising the steps:

(a) adding a suspension of magnetic glass particles in isopropanol to the lysed biological sample in a reaction vessel,
(b) incubating under such conditions that the analyte selectively binds to the magnetic glass particles,
(c) removing non-bound sample components from the reaction vessel,
(d) incubating under such conditions that the analyte is eluted from the magnetic glass particles, and
(e) separating the eluate from the magnetic glass particles.

* * * * *